United States Patent [19]

McAleer et al.

[11] 4,080,258

[45] Mar. 21, 1978

[54] CELL AND VACCINE PRODUCTION

[75] Inventors: William J. McAleer, Ambler; Raymond E. Spier, Lansdale, both of Pa.

[73] Assignee: Merck & Co., Inc., Rahway, N.J.

[21] Appl. No.: 438,082

[22] Filed: Jan. 30, 1974

Related U.S. Application Data

[63] Continuation of Ser. No. 321,095, Jan. 4, 1973, abandoned.

[51] Int. Cl.$^2$ .................. A61K 39/12; C12B 3/00
[52] U.S. Cl. ........................................ 195/1.7
[58] Field of Search .................. 195/1.1–1.8; 424/89

[56] References Cited

U.S. PATENT DOCUMENTS 3,407,120  10/1968  Weiss et al. ............... 195/104
3,839,155  10/1974  McAleer et al. ............ 195/127

OTHER PUBLICATIONS

Litwin, "Mass Cultivation of Mammalian Cells," Process Biochemistry, pp. 15–17, July 1971.

*Primary Examiner*—Shep K. Rose
*Attorney, Agent, or Firm*—Donald J. Perrella; Julian S. Levitt

[57] ABSTRACT

Production of cells and vaccines utilizing a multiplate propagator in which the fluid dynamics of the system can be controlled during the growth cycle and/or the harvesting conditions can be controlled by rapidly cooling the harvested vaccine or by using multiple harvests, with or without automated collection of the vaccine thereby producing cells and vaccines in significantly increased yields and at substantially reduced costs in comparison with presently utilized procedures.

14 Claims, 5 Drawing Figures

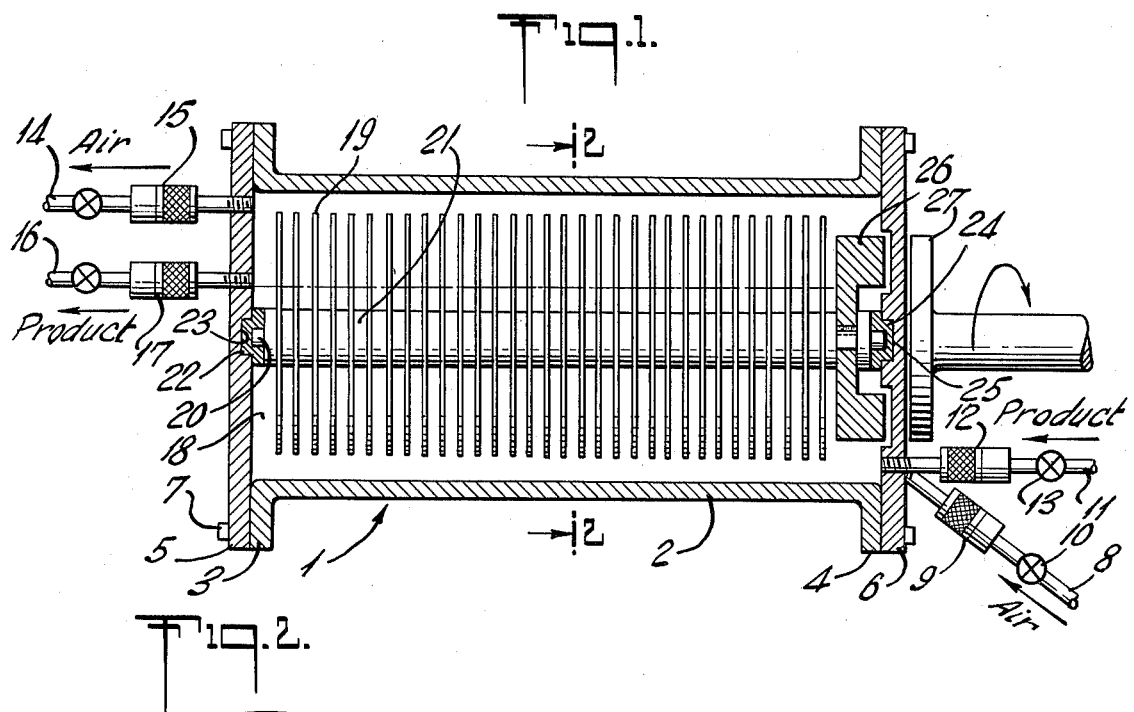
Fig. 1.
Fig. 2.
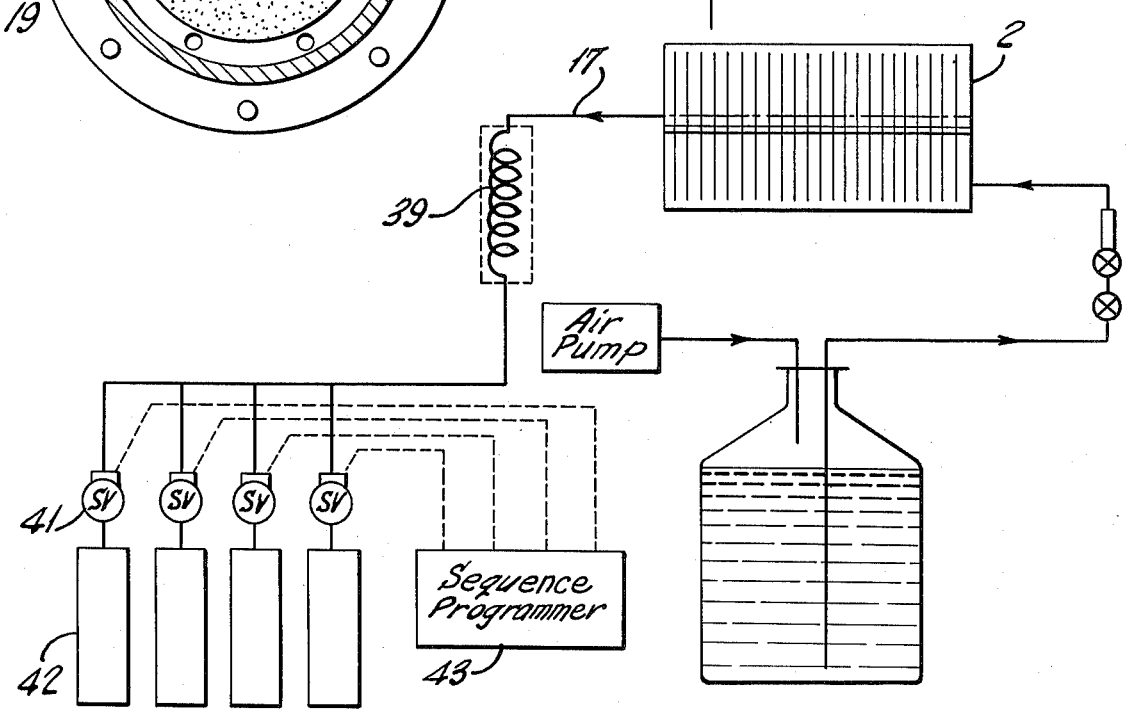
Fig. 5.

CELL AND VACCINE PRODUCTION

This is a continuation, of application Ser. No. 321,095, filed Jan. 4, 1973, now abandoned.

This invention relates to the improved production of cells and vaccines.

More particularly, this invention relates to the production of cells and vaccines employing a multiplate propagator in which the fluid dynamics of the system can be controlled during the growth cycle of a production run and/or the harvesting conditions can be controlled by quickly cooling the harvested vaccine or by multiply harvesting the vaccine, including, if desired, the automated collection of the vaccine. The use of such techniques enables one to produce cells and vaccines in significantly increased yields and at substantially reduced costs compared with presently utilized procedures.

Human and animal vaccines have been commercially produced by growing the desired virus in primary cells which must be grown on surfaces. Commercial processes were initially developed in Brockway bottles. These processes required the use of thousands of individual bottles to achieve the production of sufficient quantities of vaccine. The use of large numbers of bottles or production units is time consuming and costly, and creates a substantial risk of contamination. As production techniques evolved, the original Brockway bottles were replaced by roller bottles which only slightly reduced the number of production units and the handling problems associated therewith.

More recently, mass culture systems have been developed, as exemplified by the multiplate unit disclosed in U.S. Pat. No. 3,407,120 and the Biotec cyclindrical rotating disc apparatus. However, these units provide only minimal advantages over the original individual bottle system.

The present invention provides processes and devices for optimizing the production of cells and vaccines thereby producing cells and vaccines in significantly increased yields and at substantially reduced costs compared with presently utilized procedures.

More particularly, the present invention provides processes and devices for producing cells and vaccines in a tank system in which the methodology of nutrient supply, the fluid dynamics within the tank system and the harvesting conditions are controlled in order to optimize the system and thereby produce cells and vaccines in significantly increased yields and at substantially reduced costs in comparison with presently utilized procedures. Of particular interest are tank systems which utilize multiplate propagation. For example, in one aspect of this invention the system may be operated in the plug flow mode whereby fluids and nutrients being added to the tank are not mixed with material that is already present, but rather displace the already present material. Alternatively, the mixed flow mode may be utilized wherein the material entering the tank is rapidly dispersed throughout the tank, and uniformly mixed with the material already in the tank. In addition, in accordance with the invention the flow of nutrient material may be controlled as to produce continuous, intermittent or variable flow (including intermediate values) depending on the condition of the system.

In another aspect of this invention, the harvested vaccine is rapidly cooled and stored at low temperatures in order to prevent or significantly reduce the rate of degradation of the vaccine.

In a further feature of the invention the vaccine may be multiply harvested utilizing either automatic or manual control means.

An advantage of the present invention is the production of cells and vaccines in increased yields and at substantially reduced costs compared with presently utilized procedures.

A further advantage of the present invention is that by multiply harvesing the vaccine, preliminary screening for acceptable product can be performed on each batch harvested thereby resulting in minimizing the total cost of safety testing the final product and thereby improving the overall efficiency of the production process. This inventive concept of multiple harvests in multiplate propagators is clearly distinct from single harvest procedures wherein the total product of a production run is harvested, collected and analyzed in its entirety thereby increasing the probability that the product of the entire run be discarded if a component of the material harvested is unacceptable.

A still further advantage of the present invention is that the titre of the vaccine may be maintained at its peak by cold harvesting the vaccine, thereby increasing the yield and the overall efficiency of the process.

These and other objects and advantages of the present invention will be readily understood by reference to the following detailed description when considered in conjuntion with the accompanying drawings in which:

FIG. 1 is a cross sectional view of a typical multiplate propagator employed in the present invention;

FIG. 2 is a sectional view taken along the line 2—2 of FIG. 2;

FIG. 5 is a schematic diagram of the multiple harvesting aspects of vaccine production using the teachings of the present invention.

Figure 3:
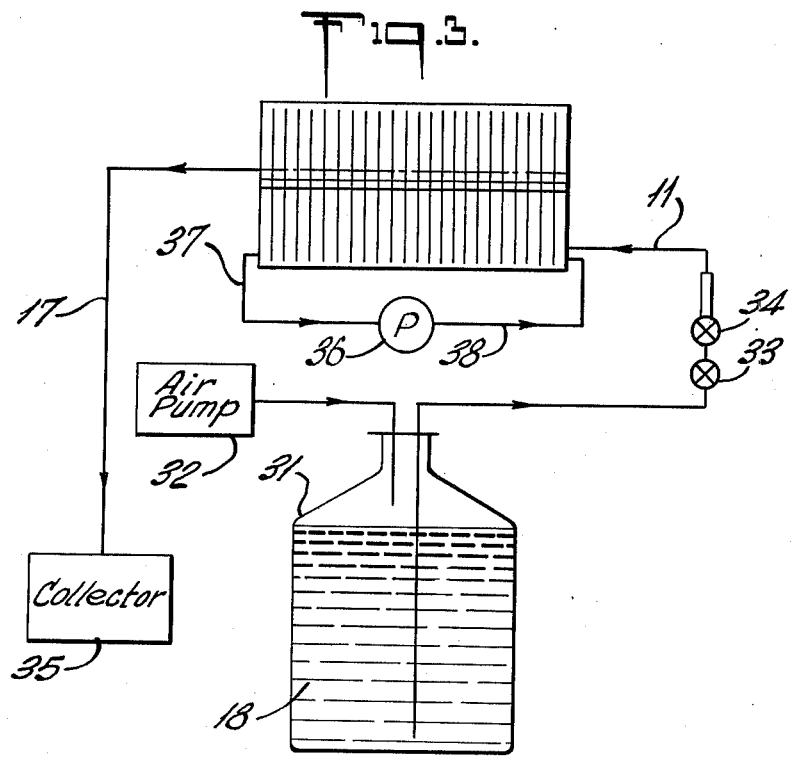
FIG. 3 is a schematic diagram of the control of the fluid dynamics of a typical multiplate propagator employed in the present invention.

Referring to FIG. 1, there is disclosed a propagator 1 which comprises a cylindrical stainless steel tank 2 having flanges 3 and 4 at each end thereof. Top and bottom plates 5 and 6 are sealed to flanges 3 and 4 by clamps 7. An air-carbon dioxide mixture is pumped into the tank 2 from a reservoir (not shown) through a line 8 which is connected to the tank by a coupling device 9 in plate 6. A valve 10 is used to control the rate of flow of this mixture to the tank. Additional medium, serum and other nutrients may be supplied to the tank through line 11 which is connected to the tank by coupling device 12. A valve 13 is used to control the rate of flow of nutrients to the tank. Outlet line 14 is connected to the tank by coupling device 15 which is in the upper portion of plate 5 in order to remove air from the tank so that the air pressure inside the tank does not build up to an unsatisfactory level. A further line 16 is connected to the tank 1 by coupling device 17 which is located slightly above the center of plate 5 in order to permit fluids to be withdrawn from the tank, thereby preventing the level of fluid or medium 18 in the tank from rising above the desired level. It is necessary to control the level of the medium in order to insure the proper aeration of the plates 19 as they rotate through the medium. The plates 19 are mounted on a bar 20, which supports the plates 19 in a separated state due to the presence of cylindrical spacers 21 between each plate. One end of the bar 20 is rotatably supported by a bearing 22 which is mounted in recess 23 in end plate 5. The other end of the bar 20 is also rotatably supported by a bearing 24 which is mounted in a recess 25 in end plate 6. A magnet 26 which is fixedly mounted on bar 20 is engaged by a second magnet 27 which is driven so as to rotate the plates 19 through the medium 18 during the cell growth and virus infection stages of operation.

FIG. 2 is a sectional view taken along line 2—2 of FIG. 1, and shows the spacing of the plates 19 from the walls of the tank 2.

FIG. 3 is a schematic diagram that depicts the control of the fluid dynamics of a typical multiplate propagator employed in the present invention in which a supply of medium 18 in a vessel 31 is fed by means of an air pump 32 through a series of control valves 33 and 34 and line 11 into the tank 2. Control valves 33 and 34 may be used to vary the flow of the nutrient mixture in such a manner that the flow may be continuous, intermittent or variable depending on the conditions of the system. The vaccine is harvested through a line 17 and collected in a collection device 35. A pump 36 connected to lines 37 and 38 is used to control the fluid dynamics of the system. When the plug flow mode is desired, the pump 36 is not utilized and the medium being added to the tank 2 through line 11 displaces the medium already in the tank. When the mixed mode is desired, the pump 36 is used to circulate the fluid in tank 2 through lines 37 and 38 and back into the tank at a rate of from about 50 to about 250 cc/min. in order to thoroughly mix the medium being added and the medium already in the tank 2. Irrespective of whether the system is being operated in the mixed or plug flow mode, the nutrient supply may be controlled by means of valves 33 or 34 so that the flow can be continuous, intermittent or variable.

Figure 4:
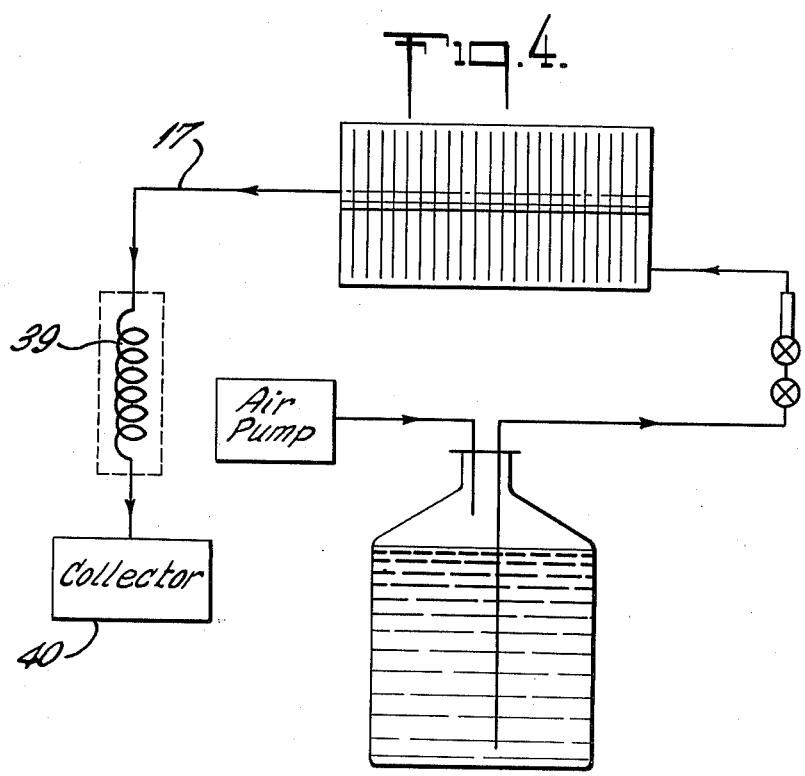
FIG. 4 is a schematic diagram of the cold harvesting aspects of vaccine production using the teachings of the present invention.

FIG. 4 is a schematic diagram that depicts the cold harvesting aspects of vaccine production using the teachings of the present invention in which the vaccine that is withdrawn from the tank 2 through line 17 is quickly passed through a cooling coil 39 and cooled to about 4° C. whereupon it is stored in a refrigerated collection device 40 until further processing.

FIG. 5 is a schematic diagram that depicts the multiple harvesting aspects of vaccine production using the teachings of the present invention in which the vaccine that is withdrawn from the tank 2 through line 17 is immediately passed through cooling coil 39 and passed through shut off valves 41 and into a multiplicity of collection vessels 42. A sequence programmer 43 may be used to automatically operate the shut off valves 41 and control the collection process.

The process and device of this invention may be used to produce viral vaccines such as mumps, measles, rubella, parainfluenza, Mareks and cells such as WI-38, chick embryo and duck embryo cells. Standard cells, sera and media may be used to produce the aforementioned vaccines. For example, primary cells such as chick embryo fibroblasts, green monkey kidney, bovine kidney, dog kidney or diploid cells such as WI-38 may be utilized as may standard sera such as fetal calf, calf, bovine, G-G-free newborn calf, $\alpha$-gamma calf or $\alpha$-gamma bovine and standard media such as Eagles Basel Medium, Medium EBME, Medium 199, and Eagle's Minimum Essential Medium.

The invention will be better understood by reference to the following examples.

EXAMPLE 1

A rotating disc propagator is charged with a mixture of 1.5 billion trypsinized chick embryo cells, Medium 199 and 45 ml. of 2.8% of $NaHCO_3$ per liter of medium and 10% fetal calf serum based upon the volume of medium. The propagator is held in the vertical position at a temperature of 37° C. until plating is effected. After three hours the fluid in the propagator is discharged and a further 1.5 billion trypsinized chick embryo cells are added to said discharged fluid and, after mixing, the fresh suspension is transferred back into the propagator which is held in the opposite vertical position to the first plating at a temperature of 37° C. By these operations both sides of the discs are plated with cells. The propagator is then positioned so that the plane of the discs is in the vertical axis and a portion of the medium and serum is discharged until the unit is about half full. The discs are then rotated at a speed of one revolution per five minutes and air or a mixture of 5% $CO_2$ and 95% air is passed through the unit at a rate of 100 cc/minute. When the growth cycle has been completed, normally 65–80 hours after planting, the spent serum and medium is discharged from the propagator and the propagator is washed with Hank's solution and recharged with fresh Medium 199, 60 ml 2.8% $NaHCO_3$ per liter of medium and 25% SPGA based upon the volume of medium, and 1 ml of a mumps virus suspension with a $-\log_{10}$ $TCID_{50}/0.1$ ml. of 3.6. The propagator is then returned to the mode in which the discs rotate and in which gas passes through it.

When the concentration of the mumps virus in the supernatant fluids has reached the desired concentration additional Medium 199, $NaHCO_3$ and SPGA is fed to the front of the tank at a fixed rate which may be between 10–100 cc/minute and vaccine is bled from the back of the tank at the same rate.

The preceding example illustrates the plug flow mode of the system.

EXAMPLE 2

A rotating disc propagator is charged with a mixture of 1.5 billion trypsinized chick embryo cells, Medium 199 and 45 ml of 2.8% $NaHCO_3$ per liter of medium and 10% fetal calf serum based upon the volume of medium. The propagator is held in the vertical position at a temperature of 37° C. until plating is effected. After three hours the fluid in the propagator is discharged and a further 1.5 billion trypsinized chick embryo cells are added to said discharged fluid and, after mixing, the fresh suspension is transferred back into the propagator which is held in the opposite vertical position to the first plating at a temperature of 37° C. By these operations both sides of the discs are plated with cells. The propagator is then positioned so that the plane of the discs is in the vertical axis and a portion of the medium and serum is discharged until the unit is about half full. The discs are then rotated at a speed of one revolution per five minutes and air or a mixture of 5% $CO_2$ and 95% air is passed through the unit at a rate of 100 cc/minute. When the growth cycle has been completed, normally 65–80 hours after planting, the spent serum and medium is discharged from the propagator and the propagator is washed with Hank's solution and recharged with fresh Medium 199, 60 ml 2.8% $NaHCO_3$ per liter of medium and 25% SPGA based upon the volume of medium, and 1 ml of a mumps virus suspension with a $-\log_{10}$ $TCID_{50}/0.1$ ml of 3.6. The propagator is then returned to the mode in which the discs rotate and in which gas passes through it.

When the concentration of mumps virus in the supernatant fluids has reached the desired concentration additional Medium 199, NaHCO$_3$ and SPGA is fed into the tank at a fixed rate which may be between 10–100 cc/minute and at the same time the mixing system is actuated by starting a pump which transfers fluid from the front end of the propagator to the back end of the propagator at a rate of 50–250 cc/minute. Vaccine is withdrawn from the system at a rate identical with the feed rate of the medium.

The immediately preceding example illustrates the mixed mode of the system.

EXAMPLE 3

A rotating disc propagator is charged with a mixture of 1.5 billion trypsinized chick embryo cells, Medium 199 and 45 ml of 2.8% NaHCO$_3$ per liter of medium and 10% fetal calf serum based upon the volume of medium. The propagator is held in the vertical position at a temperature of 37° C until plating is effected. After three hours the fluid in the propagator is discharged and a further 1.5 billion trypsinized chick embryo cells are added to said discharged fluid and, after mixing, the fresh suspension is transferred back into the propagator which is held in the opposite vertical position to the first plating at a temperature of 37° C. By these operations both sides of the discs are plated with cells. The propagator is then positioned so that the plane of the discs is in the vertical axis and a portion of the medium and serum is discharged until the unit is about half full. The discs are then rotated at a speed of one revolution per five minutes and air or a mixture of 5% CO$_2$ and 95% air is passed through the unit at a rate of 100 cc/minute. When the growth cycle has been completed, normally 65–80 hours after planting, the spent serum and medium is discharged from the propagator and the propagator is washed with Hank's solution and recharged with fresh Medium 199, 60 ml 2.8% NaHCO$_3$ per liter of medium and 25% SPGA based upon the volume of medium, and 1 ml of a mumps virus suspension with a $-\log_{10}$ TCID$_{50}$/0.1 ml. of 3.6. The propagator is then returned to the mode in which the discs rotate and in which gas passes through it.

The vaccine which is issuing from the propagator is immediately passed through a tubular heat exchanger so as to bring its temperature down to 4° C. before collection and storage.

EXAMPLE 4

A rotating disc propagator is charged with a mixture of 1.5 billion trypsinized chick embryo cells, Medium 199 and 45 ml of 2.8% NaHCO$_3$ per liter of medium and 10% fetal calf serum based upon the volume of medium. The propagator is held in the vertical position at a temperature of 37° C until plating is effected. After three hours the fluid in the propagator is discharged and a further 1.5 billion trypsinized chick embryo cells are added and, after mixing the fresh suspension, is transferred back into the propagator which is held in the opposite vertical position to the first plating at a temperature of 37° C. By these operations both sides of the discs are plated with cells. The propagator is then positioned so that the plane of the discs is in the vertical axis and a portion of the medium and serum is discharged until the unit is about half full. The discs are then rotated at a speed of one revolution per five minutes and air or a mixture of 5% CO$_2$ and 95% air is passed through the unit at a rate of 100 cc/minute. When the growth cycle has been completed, normally 65–80 hours after planting, the spent serum and medium is discharged from the propagator and the propagator is washed with Hank's solution and recharged with fresh Medium 199, 60 ml 2.8% NaHCO$_3$ per liter of medium and 25% SPGA based upon the volume of medium, and 1 ml of a mumps virus suspension with a $-\log_{10}$ TCID$_{50}$/0.1 ml. of 3.6. The propagator is then returned to the mode in which the discs rotate and in which gas passes through it.

The perfusion of liquid through the tank may not be continuous in that a volume of liquid medium may be fed into the tank followed in a short time by harvesting from the tank of an equal volume of product thereby resulting in the multiple harvesting of the vaccine. The volume harvested in each collection may be between 20 and 100% of the tank volume. The time between such medium additions and collections may be between ½ hr. – 12 hrs.

EXAMPLE 5

A rotating disc propagator is charged with a mixture of 1.5 billion trypsinized chick embryo cells, Medium 199 and 45 ml of 2.8% NaHCO$_3$ per liter of medium and 10% fetal calf serum based upon the volume of medium. The propagator is held in the vertical position at a temperature of 37° C until plating is effected. After three hours the fluid in the propagator is discharged and a further 1.5 billion trypsinized chick embryo cells are added and, after mixing, the fresh suspension is transferred back into the propagator which is held in the opposite vertical position to the first plating at a temperature of 37° C. By these operations both sides of the discs are plated with cells. The propagator is then positioned so that the plane of the discs is in the vertical axis and a portion of the medium and serum is discharged until the unit is about half full. The discs are then rotated at a speed of one revolution per five minutes and air or a mixture of 5% CO$_2$ and 95% air is passed through the unit at a rate of 100 cc/minute. When the growth cycle has been completed, normally 65–80 hours after planting, the spent serum and medium is discharged from the propagator and the propagator is washed with Hank's solution and recharged with fresh Medium 199, 60 ml 2.8% NaHCO$_3$ per liter of medium and 25% SPGA based upon the volume of medium, and 1 ml of a mumps virus suspension with a $-\log_{10}$ TCID$_{50}$/0.1 ml of 3.6. The propagator is then returned to the mode in which the discs rotate and in which gas passes through it.

Product vaccine issuing from the propagator may be collected in a number of vessels. By the use of the valve sequencer it is possible to fill individual vessels in sequence automatically. In this way, product formed during the early part of a run may be separated from that which is formed later and thereby permit differing treatments depending on the product quality. Typically 5–20 containers is sufficient for one run.

What is claimed is:

1. In a process for the production of a vaccine wherein cells are propagated in a liquid culture medium, plated on a plurality of discs, infected with a virus before harvesting, and harvested, the improvement comprising controlling the fluid dynamics of the production system by introducing fresh medium below the level of the medium already in the system whereby the medium being introduced is not aerated.

2. In a process for the production of a vaccine wherein cells are propagated in a liquid culture medium, plated on a plurality of discs, infected with a virus before harvesting, and harvested, the improvement comprising quick cooling the harvested vaccine.

3. A process as in claim 1 wherein the system is operated in the plug flow mode.

4. A process as in claim 3 wherein the flow of nutrient supply is continuous.

5. A process as in claim 3 wherein the flow of nutrient supply is intermittent.

6. A process as in claim 3 wherein the flow of nutrient supply is variable.

7. A process as in claim 1 wherein the system is operated in the mixed flow mode.

8. A process as in claim 7 wherein the flow of nutrient supply is continuous.

9. A process as in claim 7 wherein the flow of nutrient supply is intermittent.

10. A process as in claim 7 wherein the flow of nutrient supply is variable.

11. A process as in claim 2 wherein the vaccine is cooled to about 4° C.

12. In a process for the production of a vaccine according to claim 2 the improvement comprising controlling the fluid dynamics of the production system by introducing fresh medium below the level of the medium already in the system whereby the medium being introduced is not aerated and quick cooling the harvested vaccine.

13. A process according to claim 12 wherein the vaccine is cooled to about 4° C.

14. A process according to claim 12 wherein the vaccine is multiply harvested.

* * * * *